United States Patent [19]
Molino et al.

[11] Patent Number: 5,681,267
[45] Date of Patent: Oct. 28, 1997

[54] ARRANGEMENT FOR JOINING/SEPARATING DISTAL ORTHOTIC DEVICE TO/FROM PELVIC INTERFACE

[76] Inventors: Joseph L. Molino, 2 Aura Dr., Valley Cottage, N.Y. 10989; Michael Rebarber, 28 Buckingham Pl., Glen Rock, N.J. 07452

[21] Appl. No.: 731,512

[22] Filed: Oct. 15, 1996

Related U.S. Application Data

[63] Continuation-in-part of Ser. No. 419,132, Apr. 10, 1995, abandoned.

[51] Int. Cl.⁶ .................................................. A61F 5/00
[52] U.S. Cl. ............................ 602/19; 602/23; 602/24
[58] Field of Search .............................. 602/5, 12, 16, 602/20, 19, 23–26

[56] References Cited

U.S. PATENT DOCUMENTS

| | | | |
|---|---|---|---|
| 2,578,108 | 12/1951 | Thornton | 602/16 |
| 2,812,760 | 11/1957 | Miller et al. | 602/16 |
| 3,827,431 | 8/1974 | Pecorella | 602/16 |
| 3,844,279 | 10/1974 | Konvalin | 602/16 |
| 3,923,047 | 12/1975 | Chant | 602/23 X |
| 4,531,515 | 7/1985 | Rolfes | 602/16 |
| 4,672,955 | 6/1987 | Cooper | 602/16 X |
| 4,776,326 | 10/1988 | Young et al. | 602/16 |

*Primary Examiner*—Linda C. Dvorak
*Attorney, Agent, or Firm*—Lawrence G. Fridman

[57] ABSTRACT

An arrangement for adjustably joining/separating an orthotic device to/from an exterior part of human body consists of a receiving component, a base and a proximal component. The receiving component is mounted to an exterior part of human body. The base is slidably received within the receiving component. The proximal component is movable within the base in such a manner that the proximal component is linearly and rotationally adjustable about the receiving component. The proximal component is formed having a connecting element and a locking unit for locking the proximal component at a predetermined position thereof regarding the receiving component and the base.

18 Claims, 4 Drawing Sheets

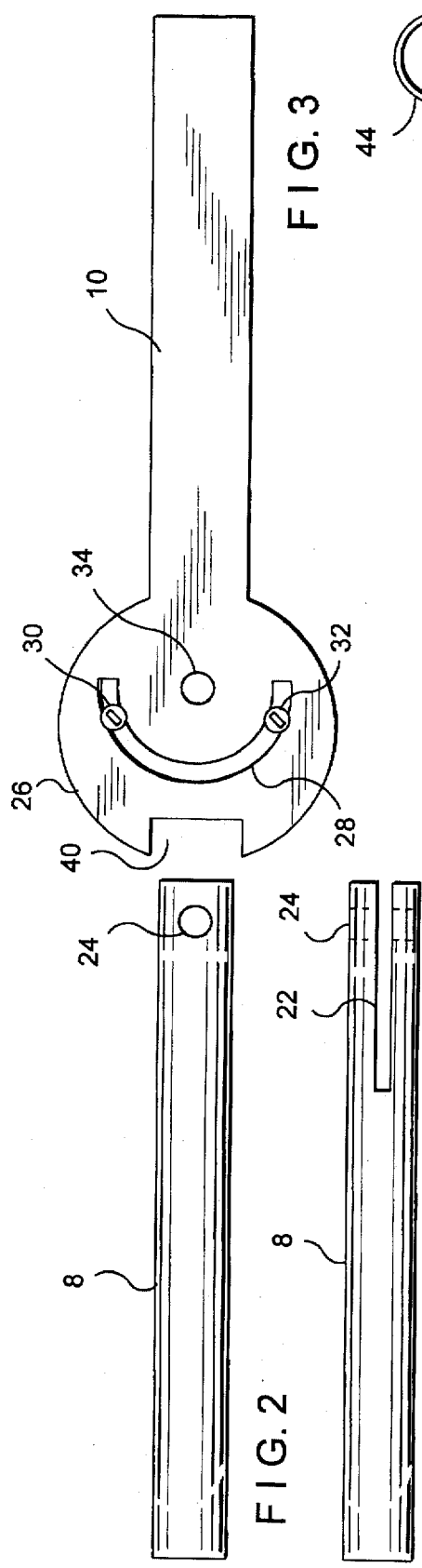

ARRANGEMENT FOR JOINING/ SEPARATING DISTAL ORTHOTIC DEVICE TO/FROM PELVIC INTERFACE

This is a Continuation-in-Part Application of U.S. patent application, Ser. No. 08/419,132 filed Apr. 10, 1995 which is now abandoned.

FIELD OF THE INVENTION

This invention relates to an arrangement which allows distal orthotic devices to be joined to and separated from exterior parts of human body. More particularly, this invention relates to the arrangement providing linear, height adjustment and internal, external rotation of the orthotic devices relative to the exterior parts of human body.

BACKGROUND OF THE INVENTION

Difficulties can arise when donning or doffing a bilateral hip abduction orthosis, i.e. a pelvic belt, with unilateral or bilateral distal components. The reasons for these difficulties include, among others, the following: a patient may have bilateral cuffs; the patient may be obese; the patient may have special donning and doffing considerations associated with fractures or surgery; successful orthotic management may involve the use of a long leg, or ischial containment fracture orthotic devices in conjunction with hip abduction; and when used with a long leg or ischial containment fracture orthotic device, height, internal and external rotation may need to be adjusted.

The present invention accommodates these and other considerations when donning and doffing a bilateral hip abduction orthosis is required.

Another important problem associated with many prior art orthotic devices in general is that adjustment and donning procedures related to these devices are often quite difficult, laborious and time-consuming. This is because a plurality of power tools such as power saws, drills, etc. are absolutely necessary for on-site, or in-hospital adjustments of unitary orthotic devices. However, in view of oxygen-safety environment, such power tools are typically not allowed there. Furthermore, metal chips resulting from use of power tools pollute hospital facilities. Therefore, among typical equipment used by orthotists for on-site adjustments of orthotic devices and allowed by hospitals are bending devices utilized for bending of hinge mechanisms. However, in view of the brittle nature of metals used and multiple bending adjustments, the metal parts of these mechanisms have often become weak and experienced metal fatigue. In view of the above factors and in order to achieve proper fitting and adjustment of orthotic devices, orthotists are forced to make many trips back and forth from hospitals to their outside facilities.

Furthermore, prior art orthotic devices allow only limited linear or height adjustments which typically cannot go beyond commonly accepted ranges. Therefore, if the required height, linear adjustment is beyond the accepted range, manufacture and/or use of an expensive custom-made orthotic hinge or device become necessary.

Another major drawback in utilizing unilateral orthotic devices is in extreme difficulties of maneuvering patients having many acute medical problems, such as broken or dislocated bones, dislocated joints, etc. Multi-unit orthotic devices having parts which can be separately positioned on a patient substantially facilitate this difficult task of medical personnel. Use of these multilateral devices is also less traumatic to patients. Utilization of multilateral orthotic devices enables medical personnel to maneuver one part of human body at a time. This is instead of maneuvering the entire body when unilateral prior art orthotic devices are used. The multilateral approach utilized by the invention also provides a much more manageable situation in terms of placing and removing orthotic devices during normal everyday care and cleaning of a patient.

Furthermore, importantly, many prior art devices do not allow rotational adjustment of the orthotic devices relative to the parts of human body, such as, for example, rotation of a leg on the axis of a hip in relation to a torso. The rotational adjustments are often absolutely necessary for proper positioning of joints and bones during the healing and treatment processes.

Thus, it has been long felt an unsolved need for multipiece orthotic devices which are capable of providing substantial linear and rotational adjustments. Furthermore, there is a need for orthotic devices capable of being adjusted at a patient's room in a hospital without utilization of power tools.

SUMMARY OF THE INVENTION

One aspect of the present invention provides an arrangement for adjustably joining/separating an orthotic device to/from an exterior part of a human body. The arrangement consists of a receiving component, a base and a proximal component. The receiving component is mounted to the exterior part of human body. The base is slidably received within the receiving component. The proximal component is mounted within the base in such a manner that the proximal component is linearly and rotationally adjustable about a longitudinal axis of the receiving component. The proximal component has a connecting element and a locking unit for locking the proximal component at a predetermined position regarding the receiving component and the base. The proximal component is releasably secured within the base. The locking unit consists of a first locking element attached to the connecting element and a second locking element. Each first and second locking elements are formed with engaging surfaces facing each other and positioned at an angle to the longitudinal axis of the proximal component. A locking member extends within the first and second locking elements, so that rotation of the locking member causes axial displacement of the locking elements relative one another, and this axial displacement locks the proximal component within the base. The rotation of the locking member causes sliding motion of one of the engaging surfaces against the other and the axial displacement of one of the locking elements about the longitudinal axis of the connecting assembly.

The first locking element and the connecting element a unitary connecting subassembly and the locking member threadably connected to the unitary connecting subassembly. The second locking element formed having a substantially hollow interior with a cross-section substantially greater than a diameter of the locking member. Upon rotation and linear advancement of the locking member toward the unitary connecting assembly, the locking member engages the second locking element causing its displacement about the longitudinal axis of the proximal component. The first and second locking elements are formed having substantially cylindrical exterior periphery. An interior portion of the base is formed having a substantially cylindrical configuration adapted to receive the substantially cylindrical exterior periphery of the first and second locking elements. The receiving component and the base are each formed with at least one aperture, so that in the assembled condition of the arrangement, the base is releasably attached to the receiving component by a pin passing through the aperture in the receiving component and the base.

A further aspect of the invention provides an arrangement for adjustably joining/separating a distal orthotic device to/from a pelvic interface. This arrangement consists of a receiving component, a base, a proximal component and a distal component. The receiving component is mounted to a pelvic interface, The base is slidably received within the receiving component. The proximal component is hingedly coupled to the distal component. The proximal component is movable within the base in such a manner that the distal component and a distal orthotic device connected thereto is linearly and rotationally adjustable about a longitudinal axis of the receiving component. The proximal component has a connecting element and a locking unit for locking the proximal component at a predetermined position regarding the receiving component and the base. The distal component is conventionally mounted to the distal orthotic device.

The locking unit consists of a first locking element attached to the connecting element and a second locking element. Each first and second locking elements are formed with engaging surfaces facing each other and positioned at an angle to the longitudinal axis of the proximal component. A locking member extends within the first and second locking elements, so that rotation of the locking member causes axial displacement of the locking element relative one another whereby the axial displacement locks the proximal component within the base.

The first locking element and the connecting element form a unitary connecting subassembly. The locking member is threadably connected to the unitary connecting subassembly. The second locking element is formed having a substantially hollow interior with a cross-section being substantially greater than a diameter of the locking member. Upon rotation and linear advancement of the locking member toward the unitary connecting subassembly the locking member presses against the second locking element causing its displacement about the longitudinal axis of the proximal component.

Another aspect of the invention provides method for joining/separating a distal orthotic device to/from an exterior part of a human body. The method consists of the following steps: mounting a receiving component to an exterior part of a human body; inserting a base with a proximal component into the receiving component; connecting the proximal component to a distal orthotic device; adjusting position of the proximal component within the base in such a manner that the distal orthotic device is linearly and rotationally adjustable about a longitudinal axis of the receiving component; and locking a predetermined position of the proximal component in the distal orthotic device about the receiving component. The proximal component includes first and Second locking elements and a locking member rotationally extending within the first and second locking elements. In the step of adjusting the rotation of the locking member causes axial displacement of the locking elements relative one another, so that the axial displacement locks the proximal component within the base.

The first locking element and the connecting member form a unitary connecting subassembly and the locking member is threadably attached to the unitary connecting subassembly. In the step of locking, upon rotation, the locking member linearly advances toward the unitary connecting subassembly engaging the second locking element and causing axial displacement of the second locking element about the longitudinal axis of the proximal component.

The method further includes the step of joining and separating the base and proximal component to and from the receiving component. This step consists of providing a hole extending through the receiving component and the base and inserting a retaining pin in the hole.

BRIEF DESCRIPTION OF THE DRAWINGS

Other advantages and features of the invention are described with reference to exemplary embodiments, which are intended to explain and not to limit the invention, and are illustrated in the drawings in which:

FIG. 2 is a plan view representation of a proximal hinge component according to the arrangement of the invention.

FIG. 3 is a plan view representation of a distal hinge component according to the arrangement of the invention.

FIG. 4 is a side view representation of the proximal hinge component.

FIG. 5 is a rear view representation of a receiving component according to the arrangement of the invention.

FIG. 6 is a side view representation of the receiving component.

FIG. 7 is an end view representation of the receiving component.

FIG. 8 is a plan view representation of a drop lock used with a hinge unit according to the arrangement of the invention including the distal and proximal hinge components.

FIG. 9 is a plan view representation of a retaining pin used for retaining the proximal and distal hinge components in a desired position.

FIG. 10 is a plan view representation of the hinge unit.

DETAILED DESCRIPTION OF THE INVENTION

Figure 1:
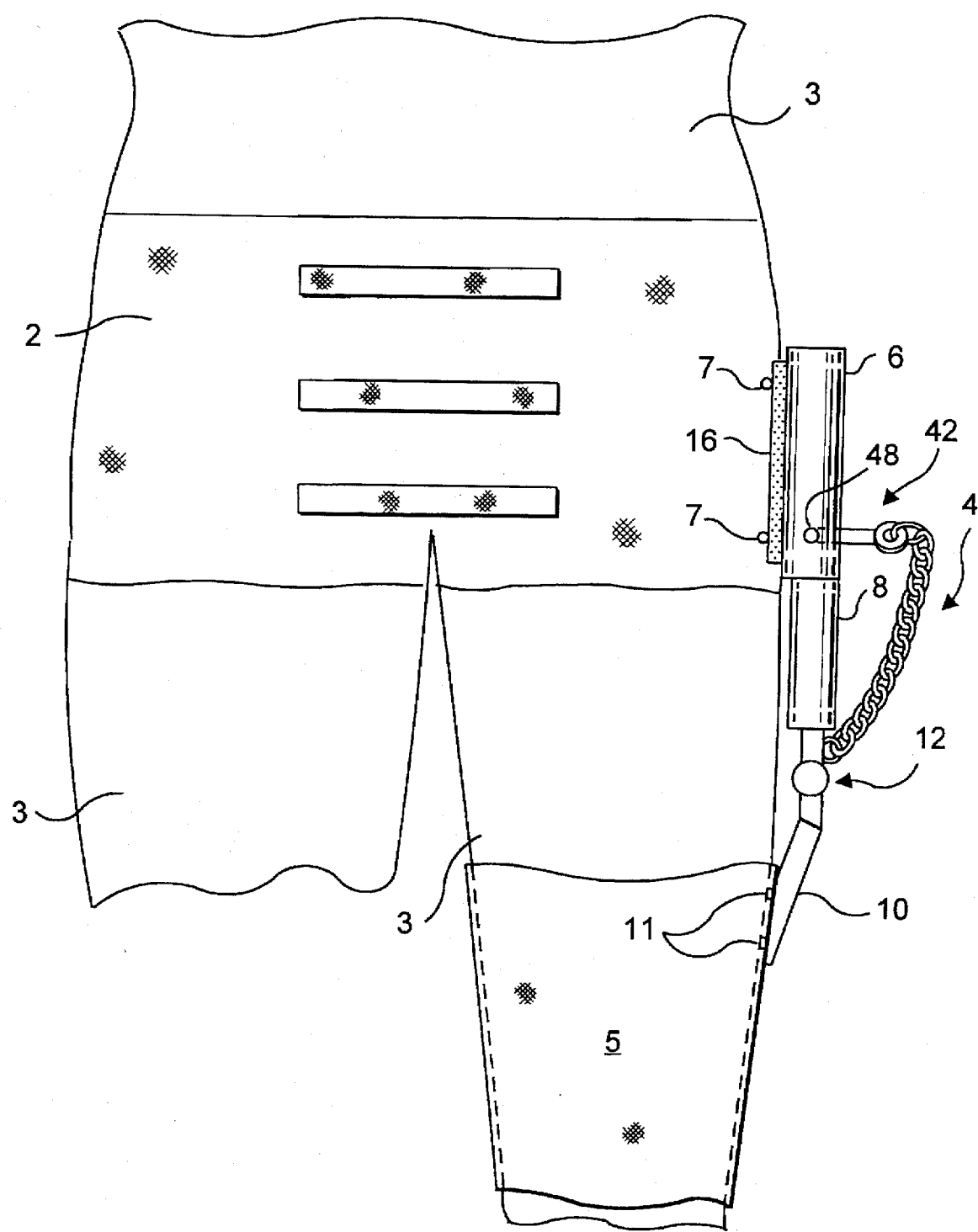
FIG. 1 is a diagrammatic representation showing the arrangement of the invention in association with a pelvic interface and a distal orthotic device.

With reference first to FIG. 1, a pelvic interface is designated by the numeral 2. Pelvic interface 2 which may be a plastic pelvic belt is worn by a patient 3 and is arranged to support a distal component, such as, for example, a thigh orthotic device 5. The present invention insures that orthotic device 5 can be easily joined to or separated from pelvic interface 2, while at the same time allowing for linear/height adjustments and internal and external rotation as well as abduction as will hereinafter be discerned.

A joining/separating arrangement according to the arrangement of the invention is designated by the numeral 4. Arrangement 4 includes a receiving component 6 which is mounted to pelvic interface 2 by suitable means such as bolts 7; a proximal hinge component 8 which fits into receiving component 6; and a distal hinge component 10 which is hingedly attached via a hinge unit 12 to proximal hinge component 8 and which is mounted by likewise suitable means 11 to distal orthotic device 5.

Receiving component 6 is in the form of a metallic tube of a material such as, for example, stainless steel having a flat member 16 attached to the rear thereof as by welding or the like as particularly shown in FIGS. 5, 6 and 7. Member 16 provides an area for a pair of holes 18 and 20. Holes 18 and 20 receive bolts 7 for fastening receiving component 6 to pelvic interface 2. This can be accomplished by, for example, threading the holes and providing a fastening point where cap bolts or the like can be placed through the pelvic interface to thereby enable said receiving component to be fastened to said interface.

Proximal hinge component 8 is in the form of a length of tubing likewise of stainless steel, for example, that has an outside diameter slightly smaller than the inside diameter of receiving component 6, thereby allowing the proximal hinge component to be inserted into the receiving component. The distal end of proximal hinge component 8 has a longitudinal slot 22 and a transverse hole 24 drilled into the proximal hinge component perpendicular to slot 22. The particular structural features of proximal hinge component 8 are illustrated in FIGS. 2 and 4.

Distal hinge component 10, particularly shown in FIG. 3, is a flat member also, for example, of stainless steel. The proximal end 26 of distal hinge component 10 is circular and has a semi-circular slot 28 formed therein. Slot 28 receives a pair of shoulder bolts or the like 30 and 32 which are effective as stops to limit flexion and/or extension, and which limit can be adjusted through an entire range of motion as required. An axle hole 34 is drilled through circular end 26 of distal hinge component 10. Abduction is accomplished by bending the flat distal hinge component as is required.

With particular reference to FIGS. 3 and 4, distal hinge component 10 is inserted into slot 22 of proximal hinge component 8, whereupon an axle 35 is removably inserted through proximal hinge component hole 24 and distal hinge component hole 34 to provide hinge unit 12 between the proximal and distal hinge components, as particularly shown in FIGS. 1 and 10.

A drop lock 36 (FIG. 8) of stainless steel, for example, is in the form of a piece of tubing and is allowed to slip past a lock-out/lock-in button 38 on distal hinge component 8 (FIG. 10) and to engage a squared notch 40 in rounded end 26 of distal hinge component 10. Lock-out/lock-in button 38 is spring loaded to prevent accidental movement of drop lock 36 into an undesired position. As will now be discerned, drop lock 36 is effective for hingedly coupling proximal hinge component 8 and distal hinge component 10 as is required for the purposes of the invention.

A retaining pin 42 is illustrated in FIG. 9. Pin 42 is a dowel-like pin with a pull ring 44 on one end thereof and a spring loaded ball 45 on the other end. Pin 42 is used to removably couple hinge unit 12 to receiving component 6 as shown in FIG. 1. A retaining chain 46 is secured to retaining pin ring 44 and to hinge unit 12.

Upon receiving component 6 being mounted to pelvic interface 2 and hinge unit 12 assembled as particularly illustrated in FIGS. 1 and 10, proximal hinge component 8 is inserted into receiving component 6. The proper height and internal or external rotation is marked and a hole 48 is drilled through receiving component 6 and proximal hinge component 8. This hole removably receives spring pin 42 which effectively locks the arrangement at a desired height and for a desired rotational displacement of the distal orthotic device 5.

Figure 11:
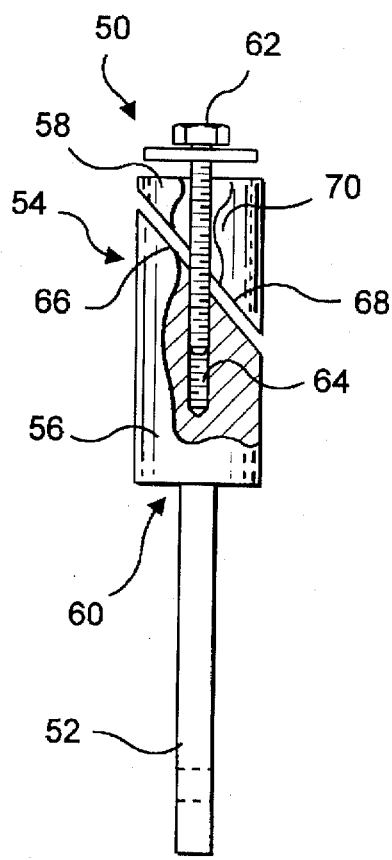
FIG. 11 is a side view representation of another embodiment of the proximal hinge component.
Figure 12:
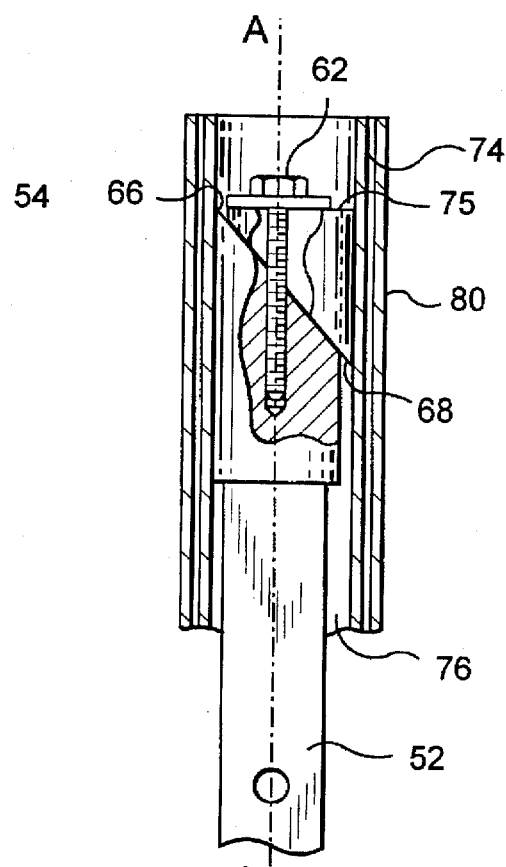
FIG. 12 is a partial cross-sectional view showing the proximal hinge component of FIG. 11 in the locked condition.
Figure 13:
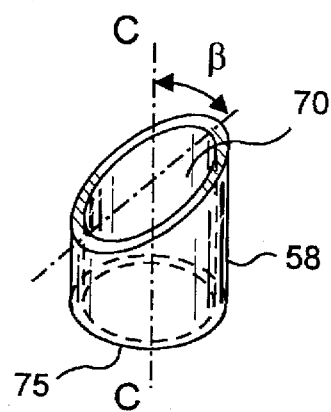
FIG. 13 is a semiperspective view showing a second locking element in an inverted position.
Figure 14:
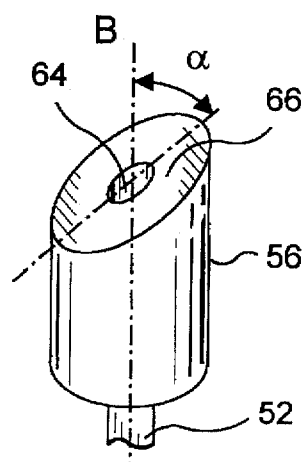
FIG. 14 is a semiperspective view showing a first locking element.
Figure 15:
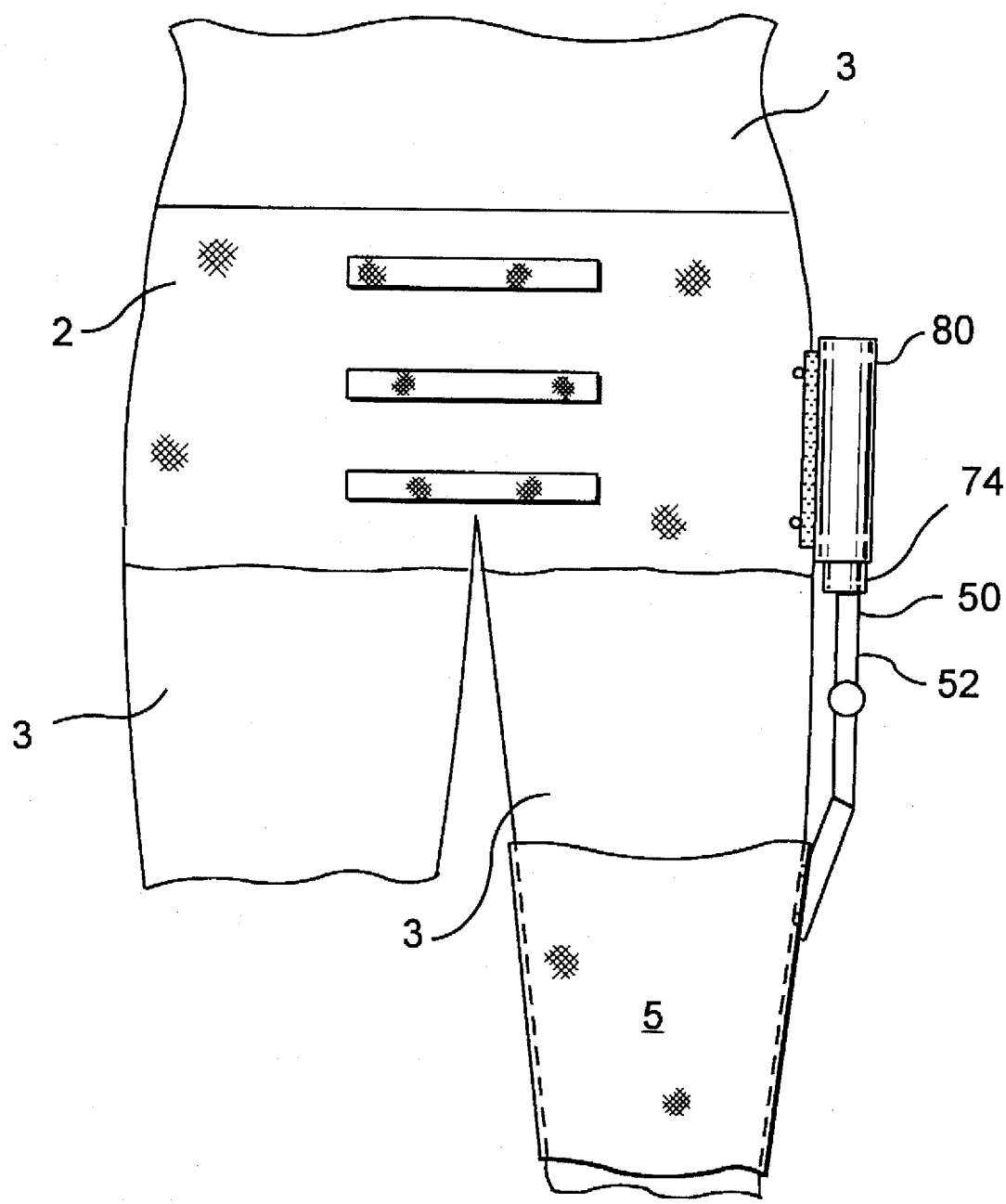
FIG. 15 is a view similar to that of FIG. 1 illustrating application of the proximal hinge component of FIG. 11.

Another embodiment of the proximal hinge component or a connecting assembly 50 of the present invention is best illustrated in FIGS. 11 and 12. The proximal hinge component or connecting assembly is adapted for receiving by the receiving component 80 through a base 74 and consists of a connecting element 52 and a locking unit 54. The connecting element is adapted for connection to a distal hinge component 84 by means of a hinge 82 (see FIG. 15) or by any other suitable connecting arrangement. The locking unit 54 which provides locking of the proximal hinge component in a predetermined position thereof within the base 74 consists of a first locking element 56, a second locking element 58 and a locking member or fastener 62. The first and second locking elements are formed having a wedge-shaped configuration with engaging surfaces 66 and 68. The engaging surface 66 is positioned at an acute angle "a" to a longitudinal axis B—B of the first locking element, whereas the engaging surface 68 is interposed at an acute angle "b" to a longitudinal axis C—C of the second locking element. The angles "a" and "b" are generally within the range between 35° and 70°. In the preferred embodiment of the invention the angles "a" and "b" are each 60°. The engaging surfaces face each other and positioned at the acute angle to a longitudinal axis A—A of the proximal hinge component in an assembled condition thereof shown in FIGS. 11 and 12. An interior area 70 of the second locking element is substantially hollow. A cross-section of this hollow interior area is substantially greater than a diameter of the locking fastener 62. As illustrated in FIGS. 11 and 12, the first locking element 56 is attached to the connecting element 52 to form a unitary connecting subassembly 60. In the assembled condition of the proximal hinge component 50 the locking fastener 62 passes through the second locking element 58 and threadably engages the unitary connecting subassembly 60. In the preferred embodiment of the invention the locking fastener 62 is adapted for threadable engagement with an elongated aperture 64 provided within the first locking element 56.

The first and second locking elements are formed having a substantially cylindrical outside periphery having a diameter slightly smaller than a diameter of an interior area of the base. Nevertheless, any suitable configuration of the outside periphery of the locking elements matching the interior of the base is within the scope of the invention.

In order to place the locking unit 54 into the interior 76 of the base, the locking fastener 62 is untightened and the exterior of the second locking element 58 is coincided with the exterior of the first locking element 56, so that the locking unit 54 resembles a continuous cylinder. In this condition, the locking unit 54 of the proximal component is positioned within the interior 76 of the base. In view of the clearance between the locking unit and the base a position of the locking unit and the proximal hinge component can be easily adjusted within the interior of the base longitudinally, linearly or rotationally.

Upon achieving a desired linear and rotational position of the proximal hinge component 50 with reference to the base 74, the proximal component is locked within the base 74 by tightening the locking fastener 62. During this action, torque applied to the locking fastener 62 is translated into its longitudinal, linear motion in the direction of the connecting element 52. Upon such movement, a head of the fastener 62 directly or indirectly, through the washer or any other suitable element, engages a front end 75 of the second locking element placing it in motion which results in a contact between the engaging surfaces 66 and 68. Further advancement of the locking fastener 62 results in sliding of the second engaging surface 68 along the first engaging surface 66 and axial displacement of the first and/or second locking elements relative to one another. It is shown in FIG. 12 that axial displacement of the second locking element 58 relative to the first locking element 56 results in a partial displacement of the outer part of the second locking element beyond the first locking element, so that the proximal component is locked within the base. The above-discussed range of the angles "a" and "b" (35°–70°) ensures good retention characteristics of the locking unit without extra torque applied to the locking fastener 62. Thus, rotational and longitudinal position of the proximal component regarding the base, connecting component and ultimately the patient's body is also locked.

In one application of the present invention, the receiving component 80 is mounted to a pelvic interface in a manner described with reference to the embodiment of FIG. 1. The proximal hinge component having the locking unit is positioned within the interior of the base which is in turn placed into the receiving component and pinned. When pin 42 is removed, the base-proximal hinge component combination can be pulled from its engagement with the receiving component. Such arrangement provides the invention with the ability to separate the lower portion of the leg brace from the upper portion thereof when necessary.

In a similar manner the device of the invention has the ability to be re-connected to the receiving component in the same position as set up originally. If it is necessary to make height, linear and/or rotational adjustment of the proximal component and other parts of the orthosis attached thereto relative to the receiving component, the locking member 62 is released in a manner described hereinabove. Upon reaching a desired linear and/or rotational position of the proximal component, the locking members of the locking unit are locked against the interior of the base. The base tube is then inserted into the receiving component and pinned (via 42) through the retaining pin hole 48 of both the base tube and receiver. This ensures that the same height, linear orientation and rotational position is repeated time after time upon removal and reassembly of the orthosis. The linear and rotational orientation of the separated parts of the orthosis remains identical every time it is separated and reassembled. If, for some reason, orientation of the elements must be changed by order of a physician or by necessity, then such change can be readily achieved simply by loosening the locking fastener 62 and unlocking the wedge-shaped locking elements from their engagement with the interior of the base tube as described hereinabove. Upon achieving a desired position of the elements, tightening the locking fastener results in locking of the locking elements inside the base tube.

Since adjustment of the invention involves only releasing and tightening the locking fastener 62 and manipulation of the pin, a technician can, without using power tools, adjust the device to accommodate individual needs of a patient in a hospital. Furthermore, this invention enables the user to separate components and create a maneuverable multi-piece orthosis instead of a large, cumbersome unilateral arrangement. Such arrangement facilitates placement of the device on a patient while she or he is in a bed.

Although the arrangement of the present invention has been described with reference to proximal and distal knee components interface of a leg brace, many other suitable applications of the arrangement are also contemplated. The device of the present invention provides linear and rotational adjustability of prosthetic devices and also enables the user to separate components of a prosthetic device, manipulate them independently and then reattach in their original position. In view of the above, the arrangement of the invention can be utilized in prosthetic devices involving practically all major joints of human body. In this respect, the arrangement of the invention can be used in prosthetic devices associated with proximal and distal components of a hip, ankle, foot, etc. For example, the arrangement of the invention can be utilized for joining and separation of proximal and distal shoulder orthosis that controls rotation and fixation of the upper shoulder to the humerus. A further example of the use of the arrangement of the invention includes its application to a lower arm brace.

There has thus been described the arrangement which facilitates successful orthotic management in general and specifically allows distal components of orthotic devices to be easily joined to or separated from parts of human body including the pelvic interface and at the same time provides adjustments of height and internal and external rotation as well as abduction.

With the above description of the invention in mind, reference is made to the claims appended hereto for a definition of the scope of the invention.

What is claimed is:

1. An arrangement for adjustably joining/separating an orthotic device to/from an exterior part of a human body, comprising:
   a receiving component, said receiving component mountable to an exterior part of human body;
   a base, said base being slidably received within said receiving component;
   a proximal component, said proximal component being movable within said base in such a manner that said proximal component being linearly and rotationally adjustable about said receiving component, said proximal component having a connecting element and a locking unit for locking of said proximal component at a predetermined position regarding said receiving component and said base.

2. The arrangement of claim 1, wherein said base being releasably secured within said receiving component.

3. The arrangement of claim 2, wherein said locking unit consists of a first locking element attached to said connecting element and a second locking element, each said first and second locking elements formed with engaging surfaces facing each other and positioned at an angle to a longitudinal axis of the proximal component, a locking member extending within said first and second locking elements, so that rotation of said locking member causes axial displacement of said locking elements relative one another, whereby said axial displacement locks said proximal component within said base.

4. The arrangement of claim 3, wherein said rotation of said locking member causes sliding motion of one of the engaging surfaces against the other and axial displacement of one of said locking elements about the longitudinal axis of said proximal component.

5. The arrangement of claim 4, wherein said first and second locking elements are formed having substantially cylindrical exterior periphery.

6. The arrangement of claim 5, wherein an interior portion of said base is formed having a substantially cylindrical configuration adapted to receive said substantially cylindrical exterior periphery of said first and second locking elements.

7. The arrangement of claim 3, wherein said first locking element and said connecting element forming a unitary connecting subassembly, said locking member being threadably connected to said unitary connecting subassembly, said second locking element formed having a substantially hollow interior, a cross-section of said hollow interior being substantially greater than a diameter of said locking member, whereby upon rotation and linear advancement of said locking member toward said unitary connecting subassembly said locking member causes the displacement of said second locking element about the longitudinal axis of said proximal component.

8. The arrangement of claim 2, wherein said receiving component and said base are each formed with at least one aperture, so that in an assembled condition of the arrangement the base is releasably attached to the receiving component by a pin passing through said at least one apertures in the receiving component and the base.

9. An arrangement for adjustably joining/separating a distal orthotic device to/from a pelvic interface, comprising:
- a receiving component, a pelvic interface, said receiving component mountable to said pelvic interface;
- a base, said base being slidably received within said receiving component;
- a proximal component hingedly coupled to a distal component, said proximal component being movable within said base in such a manner that said distal component being linearly and rotationally adjustable about said receiving component, said proximal component having a connecting element and a locking unit for locking of said proximal component at a predetermined position regarding said receiving component and said base; a distal orthotic device; and
- said distal component mountable to said distal orthotic device.

10. The arrangement of claim 9, wherein said locking unit consists of a first locking element attached to said connecting element and a second locking element, each said first and second locking elements are formed with engaging surfaces facing each other and positioned at an angle to a longitudinal axis of the proximal component, a locking member extending within said first and second locking elements, so that rotation of said locking member causes axial displacement of said locking elements relative one another, whereby said axial displacement locks said proximal component within said base.

11. The arrangement of claim 10, wherein said first locking element and said connecting element forming a unitary connecting subassembly, said locking member being threadably connected to said unitary connecting subassembly, said second locking element formed having a substantially hollow interior, a cross-section of said hollow interior being substantially greater than a diameter of said locking member, whereby upon rotation and linear advancement of said locking member toward said unitary connecting subassembly said locking member causes the displacement of said second locking element about the longitudinal axis of said proximal component.

12. The arrangement of claim 11, wherein said first and second locking elements are formed having substantially cylindrical exterior periphery.

13. The arrangement of claim 12, wherein an interior portion of said base is formed having a substantially cylindrical configuration adapted to receive said substantially cylindrical exterior periphery of said first and second locking elements.

14. A method for joining/separating a distal orthotic device to/from an exterior part of human body, comprising:
- mounting a receiving component to an exterior part of human body;
- inserting a base with a proximal component into the receiving component;
- connecting said proximal component to a distal orthotic device;
- adjusting position of the proximal component within the base in such a manner that the distal orthotic device is linearly and rotationally adjustable about said receiving component; and
- locking a predetermined position of the proximal component and the distal orthotic device about the receiving component.

15. The method of claim 14, wherein said proximal component includes first and second locking elements and a locking member rotationally extending within said first and second locking elements, whereby in said step of adjusting said rotation of said locking member causes axial displacement of said locking elements relative one another, so that said axial displacement locks said proximal component within said base.

16. The method of claim 15, wherein said first locking element and said connecting member forming a unitary connecting subassembly and said locking member being threadably attached to said unitary connecting subassembly, whereby in said step of locking upon said rotation the locking member linearly advances toward the unitary connecting subassembly engaging said second locking element causing axial displacement of the second locking element about the longitudinal axis of the proximal component.

17. The method of claim 14 further including the step of joining and separating the base and the proximal component to and from the receiving component.

18. The method of claim 17, wherein said step of joining and separating further consisting of providing a hole extending through the receiving component and the base and inserting a retaining pin in said hole.

* * * * *